(12) United States Patent
Halow

(10) Patent No.: US 8,361,452 B2
(45) Date of Patent: Jan. 29, 2013

(54) BOWEL CLEANSING COMPOSITION

(76) Inventor: George M. Halow, El Paso, TX (US)

( * ) Notice: Subject to any disclaimer, the term of this patent is extended or adjusted under 35 U.S.C. 154(b) by 492 days.

(21) Appl. No.: 10/194,251

(22) Filed: Jul. 15, 2002

(65) Prior Publication Data

US 2004/0009236 A1 Jan. 15, 2004

(51) Int. Cl.
*A61K 31/77* (2006.01)
*A61K 31/047* (2006.01)
*A61K 31/08* (2006.01)
*A61K 33/42* (2006.01)

(52) U.S. Cl. .................. 424/78.01; 424/606; 514/723; 514/738; 514/892

(58) Field of Classification Search ............ 424/78.01, 424/606; 514/892
See application file for complete search history.

(56) References Cited

U.S. PATENT DOCUMENTS

| | | | | |
|---|---|---|---|---|
| 3,330,311 | A | * 7/1967 | Christine et al. ............. | 141/167 |
| 5,498,425 | A | 3/1996 | Wood et al. | |
| 5,616,346 | A | 4/1997 | Aronchick | |
| 5,710,183 | A | 1/1998 | Halow | |
| 5,782,762 | A | * 7/1998 | Vining ........................... | 600/407 |
| 5,858,403 | A | 1/1999 | Borody et al. | |
| 5,997,906 | A | 12/1999 | Wood et al. | |
| 6,048,901 | A | * 4/2000 | Cleveland et al. ............ | 514/723 |
| 6,103,268 | A | 8/2000 | Borody et al. | |
| 6,132,767 | A | 10/2000 | Borody et al. | |

FOREIGN PATENT DOCUMENTS

WO WO 9843654 A1 * 10/1998

OTHER PUBLICATIONS

Matsuoka et al., Therapeutic Research (1996), vol. 17, Supp. 2, pp. 189 (S-413)-192 (S-416).*
Physician's Desk Reference (49th Ed. 1995), pp. 657,658,1018,1019.*
Sobrino-Faya et al., "Pre-colonoscopy Bowel Cleansing in Hospital Patients:. . . ", Gastroenterology (2002), vol. 122, No. 4, Supp. 1, pp. A-334.*
Di Palma et al., Overnight efficacy of polyethylene glycol laxative, AJG (2001), vol. 96, No. 9, Suppl., pp. S148-S149.*
STN online, file PROMT, Acc. No. 97:507624 (Robb-Nicholson, "By the way, Doctor", Harvard Women's Health Watch (Sep. 1, 1997)), Full Text.*
Afridi et al., Gastrointestinal Endoscopy (1995), vol. 41, No. 5, pp. 485-489.*
Campbell's Center for Nutrition & Wellness-Fluids and Exercise [retrieved online on Mar. 17, 2008] retrieved from the Internet <URL:http//www.campbellwellness.com/article.aspx?id=57>.*
kraftfoods.com, Jell-o—Gelatin Dessert—Sugar Free Lemon Low Calorie [retrieved online on Mar. 17, 2008] retrieved from the Internet <URL:http://www.kraftfoods.com/kf/Products/ProductInfoDisplay.htm?SiteId=1&Product=4300020136&pf=true>.*
Prather et al., Evaluation and Treatment of Constipation and Fecal Impaction in Adults, Mayo Clin. Proc. (1998), vol. 73, p. 881-887.*
Hsieh, Treatment of Constipation in Older Adults, American Family Physician (2005), vol. 72, No. 11, pp. 2277-2284.*
Gennaro, ed., Remington's Pharmaceutical Sciences (17th Ed. 1985), pp. 1460, 1461.*
Sweetman., ed., Martindale: The Extra Pharmacopoeia (33rd Ed. 2002), p. 1201.*
Drug Facts and Comparisons (2011), pp. 1949, 2015,2018, 2019, 2024, 2026, 2027.*

* cited by examiner

*Primary Examiner* — James H Alstrum Acevedo
*Assistant Examiner* — Frank Choi

(57) ABSTRACT

The invention provides a method for rapid bowel cleansing which includes the use of a mixture of polyethylene glycol and sodium phosphate(s). The method is particularly useful for preparing the bowel prior to surgery or diagnostic procedures such as colonoscopies. The invention further comprises methods for cleansing the bowel using these compositions, and bowel cleansing kits comprising these compositions.

5 Claims, 1 Drawing Sheet

Transverse| Normal

Sigmoid|

Transverse| Ulcerated mucosa

Descending| Normal

Transverse| Normal

Transverse| Normal

BOWEL CLEANSING COMPOSITION

BACKGROUND OF THE INVENTION

The invention relates to compositions for rapid bowel cleansing which are particularly useful for preparing the bowel prior to surgery or diagnostic procedures such as colonoscopies.

FIELD OF THE INVENTION

Gastrointestinal agents for regulating bowel movement can conveniently be placed into two categories: laxatives and bowel cleansers. Laxatives are formulated for long-term use, with the intention of eliminating constipation and obtaining a regular bowel function. Many laxatives work by stimulating bowel motility (peristalsis) in various ways, as by distending the gut with bulking or osmotic agents, or by directly stimulating the bowel nerves or muscles with stimulant laxatives. Other laxatives function as stool softeners or lubricants. The various types of laxatives are often combined in attempts to maximize efficacy or to reduce side effects of the agents.

Bowel cleansers, also called purgatives, cathartics, and lavages, are formulated for rapid emptying of the bowel and are intended for short-term use only. They are commonly used as "bowel preps" for emptying the bowel prior to surgery, childbirth, or diagnostic procedures, and usually comprise an osmotic or stimulant laxative administered by either oral or anal route. While purgatives formulated for patient use as enemas are often prescribed before examinations, they are awkward to handle and are frequently not properly administered, so orally administered preparations are generally preferred. However, the orally-administered compositions for rapid bowel cleansing in common use also have disadvantages which discourage patient compliance.

DESCRIPTION OF RELATED ART

The most commonly prescribed oral bowel preps today for bowel examination include sodium phosphate compositions in varying proportions of mono- and dibasic species, and polyethylene glycol (PEG) in combination with electrolytes.

Sodium phosphate is a saline osmotic laxative, sold, for example, as Fleet Phospho-Soda® (C.B. Fleet Co., Lynchburg, Va.), which contains both monobasic and dibasic uncoated sodium phosphate powders. It is also sold as Visicol™, which includes mono- and dibasic sodium phosphates in tablet form. This laxative, when formulated and used as a bowel cleanser, is associated with nausea, vomiting, and symptoms of electrolyte imbalance; the product also has an unpleasant taste. As a result, patient compliance is difficult to obtain, particularly when the bowel cleanser is supplemented with, for example, another saline agent such as a magnesium salt, or a bowel stimulant such as bisacodyl.

While PEG is known for its successful use as a long-term osmotic laxative in combination with dietary fiber (as described in U.S. Pat. No. 5,710,183, issued Jan. 20, 1998 to Halow, and incorporated herein by reference), PEG purgatives such as Colyte® (Braintree Laboratories, Braintree, Mass.) have poor patient compliance. They have an unpleasant taste, and the amount and frequency of fluid the patient is required to drink, typically 8 fluid ounces every ten minutes over several hours, frequently cause severe bloating and attendant nausea. Further, although these purgatives normally include electrolytes to counterbalance electrolyte loss during treatment, symptoms of electrolyte imbalance are, notwithstanding, often experienced by the patient.

SUMMARY OF THE DISCLOSURE

The invention accordingly provides dry bowel cleansing compositions for oral administration including polyethylene glycol; dibasic sodium phosphate; and, optionally, monobasic sodium phosphate; which are dissolved in an aqueous carrier prior to use. For added potency in certain clinical applications a bowel stimulant such as bisacodyl, or other agent known for its laxative properties may be taken in conjunction with the administration of these compositions as appropriate.

The invention further provides methods for the short-term use of the compositions as cathartics in emergency situations or in severe constipation, or as bowel preparations prior to surgery, bowel examinations, childbirth, or similar occasions.

The demonstrate significantly improved patient compliance and very good efficacy.

DETAILED DESCRIPTION OF THE EMBODIMENTS

Figure 1:
FIGS. 1-6 are video photographs taken during colonoscopy of six different patients, illustrating the clean-out of various sections of their colons using a bowel prep according to the invention.

Polyethylene glycols useful in the composition of the invention broadly include any food-grade or pharmaceutical-grade PEG. Currently preferred for convenience of use in preparing and using the composition of the invention are PEG polymers having molecular weights above about 900 which are solid at room temperature and soluble in or miscible with water. Polymers having average molecular weights between about 3000 and 8000 are exemplary; PEG 4000, which is nearly odorless and tasteless and widely available in USP grade, or PEG 3350, are very suitable. A proprietary laxative, MiraLax® (Braintree Laboratories, supra), is a useful source of PEG 3350 powder readily soluble in water. Other suitable PEG powders are commercially available, as from the Spectrum Chemical Mfg. Company, Gardena, Calif. Non-powdered PEG should be comminuted to a particle size that is readily soluble in water before use.

The sodium phosphate powder according to the invention includes a pharmaceutical-grade (USP) free flowing powder of anhydrous dibasic sodium phosphate ($Na_2$, $HPO_4$, disodium phosphate), optionally in combination with monobasic sodium phosphate monohydrate ($NAH_2PO_4H_2O$, monosodium phosphate), or anhydrous, such as conventionally used in saline laxatives, for example, the powders described in the Fleet Phospho-Soda® composition discussed supra. The phosphate powder provides the compositions of the invention with a saline hypo osmotic effect which complements the effect of the PEG component and is used in amounts which provide the desired hypo osmolarity for this purpose, as known in the art.

To administer, the phosphate and PEG powders are simply dissolved by mixing into any desired aqueous carrier, such as water or juice.

PEG and phosphate powder are combined in amounts which provide a composition that will preferably evacuate the bowel in the course of a few (3-4) hours. Typically, a dry prep composition according to the invention will contain about 60% to 80% by weight PEG and 20% to 40% by weight of phosphate; the term "phosphate" herein refers to either disodium phosphate alone, or disodium phosphate in combination with monosodium phosphate. In typical embodiments, the amount of PEG in a composition according to the invention will be about 70% to 80% by weight, and 20% to 30% by weight sodium phosphate, based on the total amount of PEG and phosphate; the combined PEG and phosphate should make up no less than about 80% by weight of a composition containing additives for optimum results. Compositions containing about 75% to 80% by weight PEG and 20% to 25% by weight phosphate are particularly contemplated. Generally, at least a major amount (greater than about 50% by weight) of the phosphate present is disodium phosphate; if monosodium phosphate is included in the composition, it should usually make up less than one-half, and preferably less than one-quarter, of the phosphate content of the composition.

To formulate a convenient single dosage drink, a dry prep composition containing from about 45 to 70 grams powdered PEG and 10 to 30 grams phosphate powder, preferably about 55 to 65 grams PEG and 15 to 25 grams phosphate powder, is dissolved or suspended in an aqueous liquid of choice, such as water, tea, or juice. In an exemplary drink formulation, a single dose dry prep composition containing from about 58 to 63 grams PEG and from about 15 to 20 grams phosphate powder, for example, 60 grams powdered PEG and 18 grams sodium phosphate powder, preferably disodium phosphate powder, is dissolved in about 1 to 1.5 quarts of water or other aqueous liquid, for oral ingestion. Alternately, the compositions can be dissolved in a smaller portion of water, such as eight fluid ounces, and the remainder of the liquid taken in conjunction with this solution. The amount of water or other aqueous medium in which the dry prep composition is dissolved or which is taken with the dry prep composition is not critical; however, for optimum bowel cleansing, at least about a pint should be used, and preferably at least a quart, depending upon the patient's total liquid intake during the treatment.

In another embodiment of the invention, lower molecular weight PEG polymers such as PEG 400 which are liquid at room temperature may be used as a base, and the phosphate powder dissolved or dispersed therein; the solution may then be diluted to taste with the desired aqueous liquid.

The single dosage drinks so prepared are taken from twice per day to four times per day on the day preceding the colonoscopy or other procedure, depending upon the degree of clean-out required and the presence of complicating bowel conditions such as constipation. Typically, in an average patient, twice per day for one day will provide the desired result. If, for example, the patient has failed a standard prep, a two day prep is recommended. Preferably, the patient is restricted to a clear liquid diet while on the regimen, i.e., a diet of liquids containing no significant solid material. Suitable clear liquids include apple juice, tea, plain Jello®, 7-Up®, Sprite®, and chicken or beef broth. If the patient receives a sufficient amount of liquids containing sodium and potassium ions to satisfy hunger, no supplemental electrolytes need be used with the PEG/phosphate compositions.

For added potency in certain clinical applications, the compositions may be taken in conjunction with a bowel stimulant such as bisacodyl, generally available over-the-counter as Dulcolax®, BiscoLax®, or other proprietary product. For use with the present invention, bisacodyl should not be taken in powder form to avoid neutralization with stomach acids. Enterin-coated 10 milligram tablets once or twice a day are suitable.

The compositions may include, or can be taken in conjunction with, conventional additives such as flavoring or coloring agents. While not presently recommended, an herbal bowel stimulant such as Cascara sagrada may also be included in or taken in conjunction with the inventive compositions. Additionally, psyllium or other fiber commonly used as a stool bulking agent may be optionally added to or taken with the compositions, both for its laxative properties and its potential ability to counteract any adverse effects of the other components.

EXAMPLES

Methods and Materials

Patients were prepared for colonoscopy with a dry prep composition of 60 grams PEG powder and 18 grams disodium phosphate powder per dose.

Each patient was given two single-dose packets for self-administration on the day preceding the colonoscopy, with instructions to dissolve each dose in water and drink the first dose at 10 a.m. and the second at 4 p.m. For each patient, a clear liquid diet was prescribed for that day. A flavor packet containing powdered Crystal Light® Iced Tea was provided for use as desired with the prep to encourage drinking.

Results:

The results reported here are representative of those obtained in the experimental group.

Patient #1:

This is a 61 year-old female with weight loss and decrease in appetite. She underwent a clear liquid diet the day before with bowel prep taken at 10 a.m. and at 4 p.m. Good prep and adequate view of the colon was verified by multiple photographs during colonoscopy. She had no complaints of cramping or complaints of nausea. Mild dislike of taste. View of transverse colon, FIG. 1.

Figure 2:
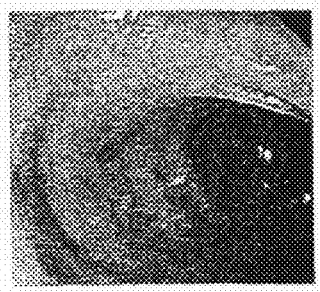

Patient #2:

This is an 86 year-old female with a history of anemia who underwent bowel prep, taking it twice the day before examination with a clear liquid diet. There was adequate clean out and a good view of the entire colon with no abnormalities found in the colon. View of sigmoid colon, FIG. 2.

Figure 3:
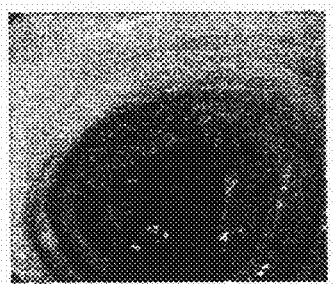

Patient #3:

This is a 62 year-old male with hemorrhoidal bleed undergoing colonoscopy. Bowel prep at 10 a.m. and 4 p.m. and a clear liquid diet were prescribed. He had no complaints of nausea, vomiting, or discomfort, No complaints of taste abnormalities He was given a flavor packet to use as needed. View of transverse colon, FIG. 3.

Figure 4:
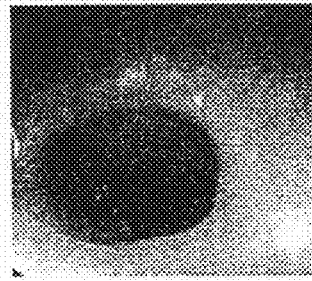

Patient #4:

This is a 74 year-old male with a history of colon polyps. for surveillance colonoscopy, underwent bowel prep and clean out the day before using the dry prep at 10 a.m. and 4 p.m. with one Dulcolax 10 milligram tablet. Adequate clean out showing diverticulosis in at the sigmoid colon. Mild rectal irritation and inflammation with a good view of the entire colon verified by video photographs taken during colonoscopy. Tolerance of the prep and slight complaint about taste, but no crampy sensation. No nausea and vomiting that he has had with other preps. View of descending colon, FIG. 4.

Figure 5:
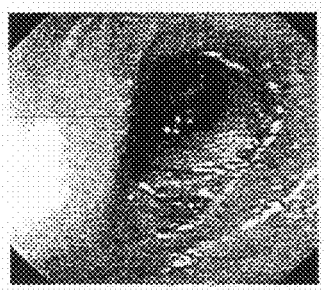

Patient #5:

This is a 50 year-old female with a first degree relative with colon cancer who underwent surveillance colonoscopy. Took the bowel prep at 10 a.m. and 4 p.m.; some stool found in the sigmoid colon. There was no liquid, able to suction out completely and got a good visualization of the entire colon verified by video photographs during the colonoscopy. with the patient having no complaints of product tolerance. No nausea and, no vomiting, with diarrhea, and no crampy sensation. View of transverse colon, FIG. 5.

Figure 6:
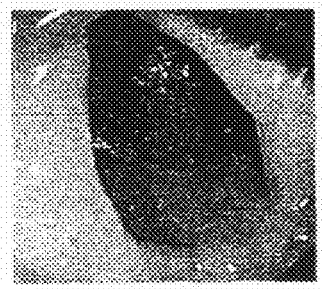

Patient #6:

This is a 50 year-old female who presented with diarrhea for colonoscopy. The bowel prep completed was taken at 10 a.m. and 4 p.m. on the day before the exam, with a clear liquid diet. The bowel prep was good, with adequate view of colon. No complaints. View of transverse colon, FIG. 6.

While the foregoing invention has been disclosed according to its various embodiments, the disclosed invention shall be described according to the scope and meaning of the appended claims.

What is claimed is:

1. A single dosage of a dry bowel cleansing composition comprising about 18 grams of a water soluble sodium phosphate powder, and about 60 grams of a water soluble PEG powder, wherein the composition contains no additional electrolytes.

2. The dry bowel cleansing composition of claim 1, wherein said water soluble sodium phosphate powder is dibasic.

3. A single dosage of a dry bowel cleansing composition comprising from about 10 grams to about 30 grams of a water soluble sodium phosphate powder and from about 45 grams to about 70 grams of a water soluble PEG powder, wherein the composition contains no additional electrolytes.

4. The single dosage of a dry bowel cleansing composition as defined in claim 3 wherein the amount of the water soluble sodium phosphate powder ranges from about 15 grams to about 20 grams and the amount of the water soluble PEG powder ranges from about 58 grams to about 63 grams.

5. The dry bowel cleansing composition of claim 3, wherein said water soluble sodium phosphate powder is dibasic.

* * * * *